United States Patent [19]

Lauer et al.

[11] 3,969,337
[45] July 13, 1976

[54] CHROMATOGRAPHIC FRACTIONATION OF WHEY

[75] Inventors: Karl Lauer, Schriesheim; Georg Stoeck, Mannheim-Waldhof; Friedrich Bätz, Lampertheim, all of Germany

[73] Assignee: Boehringer Mannheim G.m.b.H., Mannheim, Germany

[22] Filed: Mar. 27, 1974

[21] Appl. No.: 455,484

[30] Foreign Application Priority Data

Apr. 18, 1973 Germany............................ 2319581

[52] U.S. Cl............................. 260/112 R; 260/121; 260/122
[51] Int. Cl.²............................................ A23J 1/20
[58] Field of Search................. 260/112 R, 121, 122

[56] References Cited

UNITED STATES PATENTS

| | | | |
|---|---|---|---|
| 2,446,913 | 8/1948 | Erlich............................ | 260/112 R |
| 2,669,559 | 2/1954 | Reid................................ | 260/112 R |
| 3,049,530 | 8/1962 | Rackis et al. .................... | 260/123.5 |
| 3,069,327 | 12/1962 | Eldridge et al. ............. | 260/123.5 X |
| 3,154,531 | 10/1964 | Yoshimura et al. ............. | 260/123.5 |
| 3,234,199 | 2/1966 | Reid................................. | 260/112 |
| 3,298,925 | 1/1967 | Mosbach............................ | 260/112 |
| 3,547,900 | 12/1970 | Dienst et al........................ | 260/112 |
| 3,637,643 | 1/1972 | Wingerd...................... | 260/112 R X |
| 3,697,419 | 10/1972 | Grant..................................... | 210/27 |
| 3,759,826 | 9/1973 | Felicetta et al. ................ | 260/112 R |
| 3,838,143 | 9/1974 | Grant.............................. | 260/112 R |

OTHER PUBLICATIONS

Biochimica et Biophysica Acta, 100(1965) 154–162, Groves Dissertation Abstracts, Morrison, vol. 23, 1962.
Chem. Abstracts, vol. 64, 1966, 10171c–10171e, Szuchet et al.
Chem. Abstracts, vol. 54, 1960, 23102i–23103c, Schober et al.
Biochimica et Biophysica Acta, 214(1970) 419–426, Armstrong et al.
Advances in Protein Chemistry, 1967, p. 142, McKenzie.
Lab Manual of Analytical Methods of Protein Chem. vol. I, pp. 67–78, Alexander.

*Primary Examiner*—Howard E. Schain
*Attorney, Agent, or Firm*—Burgess, Dinklage & Sprung

[57] ABSTRACT

The process for the chromatographic fractionation of whey comprising passing whey through a column of an ion exchange material, thereafter passing water through said column as eluant, and collecting the aqueous effluent from said column as a plurality of fractions. Advantageously the ion exchange material is a polystyrene resin containing sulfonic acid groups neutralized with calcium ions and cross-linked with about 2 to 4% by weight of divinyl-benzene, and the eluant is demineralized water.

8 Claims, No Drawings

CHROMATOGRAPHIC FRACTIONATION OF WHEY

The present invention is concerned with a process for the chromatographic fractionation of whey.

The solids content of liquid whey is about 7%, of which about 5% is lactose, 0.9% is proteins and 0.5 – 1% is mineral salts. Sour whey contains somewhat less lactose but, in place thereof, more lactic acid.

As is known from numerous publications, whey protein is of extraordinary importance for human nutrition and experimental plants for the separation of lactalbumin and lactoglobulin have already been set up throughout the world. Generally, it is important to avoid a heat treatment of the whey in order to be able to obtain the protein in a native state. For the separation of the proteins, there have previously been used reversible osmosis, electrodialysis and fractionation with the use of a molecular sieve, for example "Sephadex". This latter process is the subject matter of U.S. Patent Specification No. 3,547,900. Without doubt, column chromatography with the use of a molecular sieve is indicated for such a separation because molecular sieves are able to distinguish very easily between large and small molecules.

Surprisingly, we have now found that the separation of whey or of a whey concentrate into the components protein (lactalbumin or lactoglobulin), lactose and salts, such as calcium lactate, takes place even more effectively on a suitable ion exchanger.

Thus, according to the present invention, there is provided a process for the chromatographic separation of whey, wherein whey is chromatographed on an ion exchanger, using water as the eluant.

Examples of ion exchangers which can be used for the process according to the present invention include polystyrene resins containing sulfonic acid groups (cation exchangers). The ion exchangers used have preferably been converted into neutral form by means of suitable cations, preferably by calcium cations.

Ion exchangers, for example polystyrene resins, are especially preferred which have a low degree of crosslinking, e.g. those corresponding to a divinyl-benzene content of about 2–4% by weight being especially preferred.

As eluant, it is especially preferred to use water which has been demineralized, if necessary.

The effective separation of the solid components present in whey with the help of the process according to the present invention is surprising because ion exchangers, in contradistinction to molecular sieves, cannot themselves distinguish between large and small molecules. It is also surprising that no denaturing takes place on the exchangers and thus an irreversible bonding of the protein does not occur. As a result of these surprising discoveries, there are obtained the following advantages for a large-scale utilization of the new process according to the present invention:

1. The contamination of sewage and waste water disposal systems by dairies is an extraordinarily important problem for the protection of the environment. It can be substantially avoided in an economic manner by the use of a separation plant operating according to the process of the present invention.

2. According to previously known methods, whey is first concentrated in order to separate out crystalline lactose. This step is now superfluous since the separation of lactose takes place in one step on the ion exchanger.

3. The thermolabile protein is separated in a very gentle manner and is obtained in the form of a pale, water-soluble product.

4. Inorganic salts and calcium lactate are also separated in an excellent manner.

5. At a given flowthrough rate, the pressure drop along the ion exchanger is considerably less than in the case of the use of a column of a molecular sieve, so that it is possible to operate on a large scale with higher throughput rates.

6. Since elution is carried out with water, the separation column can, without further treatment, be used immediately for the next cycle.

The following Example is given for the purpose of illustrating the present invention:

Example 6 liters of sour whey having a solids contents of 7.2% by weight are concentrated in a vacuum at 40°C to a six-fold solids concentration. This concentrate (about 1000ml) is applied at 20°C to a separation column of 10 cm diameter and 4 m length. The column is filled with a cation exchanger (polystyrene resin containing sulfonic acid groups: Lewatite TSW-40), which is quantitatively loaded with calcium ions. The resin, prior to sulfonation, was produced by polymerizing styrene with 4% by weight of divinyl-benzene as cross-linking agent.

10 Liters of demineralized water are run through the column at 20°C and then fractions are collected with the next 22 liters of water. The composition of the fractions is given in the following Table:

TABLE

| eluate (liters) | protein (g) | lactose (g) | intermediate runnings (g) | calcium lactate (g) |
|---|---|---|---|---|
| 10–13.5 | 48.4 | — | — | — |
| 13.5–19 | — | 284 | — | — |
| 19–26 | — | — | 17 | — |
| 26–32 | — | — | — | 82 |

The protein fraction is gently evaporated in a vacuum at 40°C. The resultant product, which is obtained in the form of almost colorless flakes, is completely water-soluble.

The lactose (284 g) is, after concentration, obtained in crystalline form.

The column is directly ready for another cycle of fractionation.

The rate at which the whey or its concentrate percolates through the column may be varied widely but preferably is such that the residence time in the column is at least about 1 hour and preferably at least about 4 hours.

It will be appreciated that the instant specification and examples are set forth by way of illustration and not limitation, and that various modifications and changes may be made without departing from the spirit and scope of the present invention.

What is claimed is:

1. The process for the chromatographic fractionation of dairy whey containing lactose, proteins and mineral salts into a protein fraction comprising passing said whey through a column of a cation exchange material in neutral form, said cation exchange material comprising a polystyrene resin containing sulfonic acid groups, thereafter passing an aqueous eluant consisting essentially of water through said column, and collecting a plurality of sequential aqueous effluents from said column as a plurality of separate fractions.

2. The process according to claim 1, wherein the ion exchange material is a polystyrene resin containing sulfonic acid groups.

3. The process according to claim 1, wherein the cation exchange material is neutralized with calcium ions.

4. The process according to claim 1, wherein the ion exchange material used has a low degree of cross-linking.

5. The process according to claim 1, wherein the ion exchange material used has a divinyl-benzene content of about 2 to 4% by weight.

6. The process according to claim 1, wherein the eluant is demineralized water.

7. The process according to claim 1, wherein the whey is concentrated before passage through the column.

8. The process according to claim 7, wherein the ion exchange material is a polystyrene resin containing sulfonic acid groups neutralized with calcium ions and cross-linked with about 2 to 4% by weight of divinyl-benzene, and the eluant is demineralized water.

* * * * *